United States Patent [19]
Toth

[11] Patent Number: 6,141,402
[45] Date of Patent: Oct. 31, 2000

[54] METHODS AND APPARATUS FOR DOSE VERIFICATION IN AN IMAGING SYSTEM

[75] Inventor: Thomas L. Toth, Brookfield, Wis.

[73] Assignee: General Electric Company, Milwaukee, Wis.

[21] Appl. No.: 09/140,109

[22] Filed: Aug. 25, 1998

[51] Int. Cl.[7] .................................................. G21K 1/04
[52] U.S. Cl. ............................................................ 378/150
[58] Field of Search .............................. 378/97, 108, 147, 378/150, 151, 152, 19, 16, 207

[56] References Cited

U.S. PATENT DOCUMENTS

| | | |
|---|---|---|
| 4,872,188 | 10/1989 | Lauro et al. . |
| 4,991,189 | 2/1991 | Boomgaarden et al. . |
| 5,982,846 | 11/1999 | Toth .......................................... 378/19 |
| 6,056,437 | 5/2000 | Toth ......................................... 378/205 |
| 6,061,419 | 5/2000 | Hsieh ........................................... 378/4 |
| 6,061,420 | 5/2000 | Strong ......................................... 378/4 |

*Primary Examiner*—Frank G. Font
*Assistant Examiner*—Gioacchino Inzirillo
*Attorney, Agent, or Firm*—Armstrong Teasdale; Christian G. Cabou; Phyllis Y. Price

[57] ABSTRACT

The present invention, in one form, is a system which, in one embodiment, utilizes signals from a detector array to verify system dose. More specifically, the detector array signal intensities are used to determine image noise and a collimator aperture to verify an x-ray dosage. Particularly, in one embodiment, the signals intensities from the detector array are used to determine the position of collimator cams. Using the position of the collimator cams, the aperture of the collimator is determined so that X-ray dose may verified using the collimator aperture and image noise information.

26 Claims, 5 Drawing Sheets

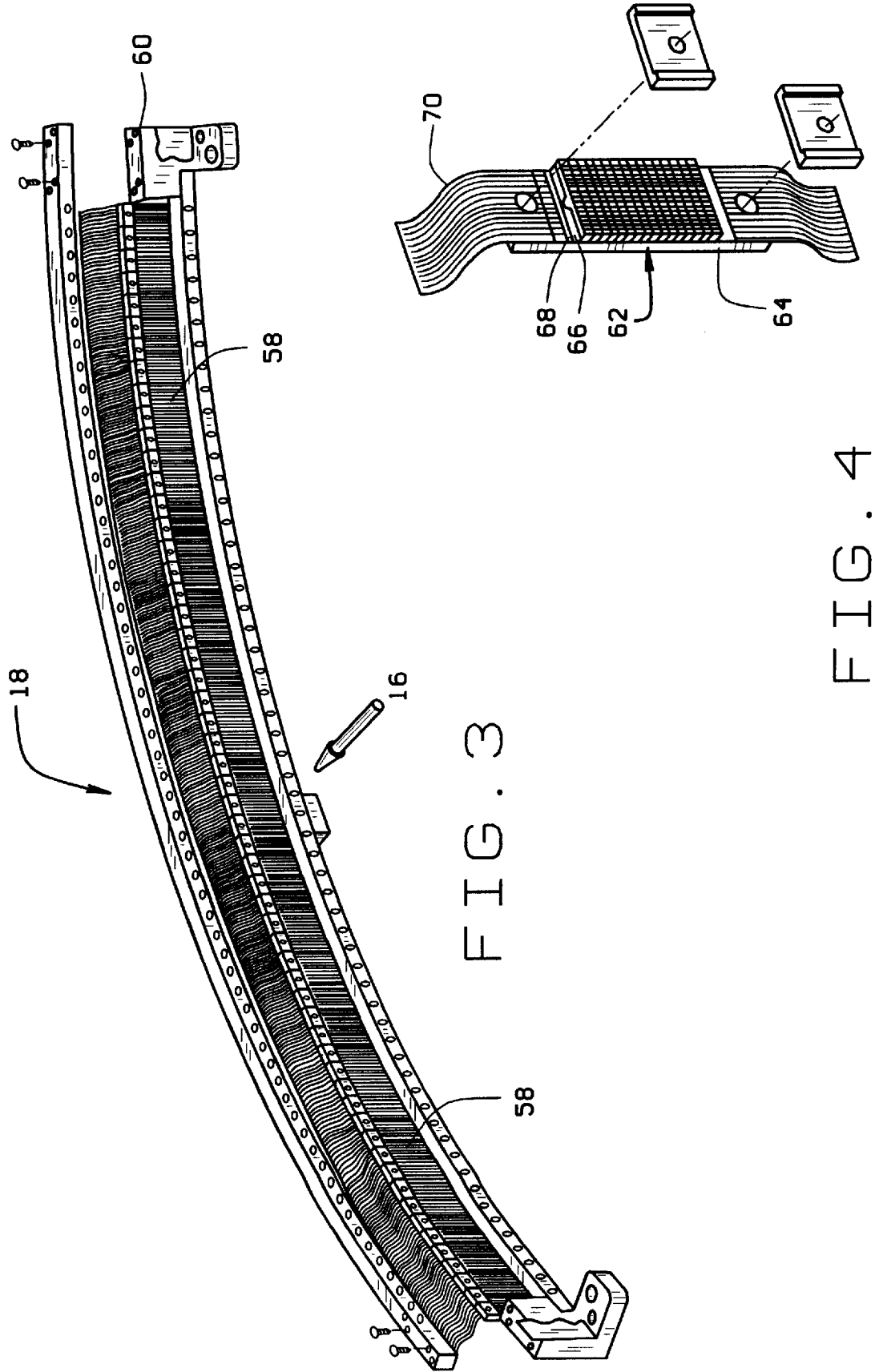

6,141,402

METHODS AND APPARATUS FOR DOSE VERIFICATION IN AN IMAGING SYSTEM

BACKGROUND OF THE INVENTION

This invention relates generally to computed tomography (CT) imaging and more particularly, to dose verification in an imaging system.

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts that attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

Certain safety tests are typically required to be completed prior to delivering, after delivery, and when certain components are replaced. One such test is verification of the x-ray dose received by an object or patient. In at least one known CT system, where the same reference object is scanned, the detector intercepts all of the direct x-ray exiting from the source collimator, and the detector x-ray energy sensitivity and gain are reasonably flat, the imaging system can be considered a dosimeter. As a result, image noise can be used for dose verification. If, however, the three described conditions are not met, for example, where a portion of the direct x-ray beam is not received by the detector, x-ray dosage cannot be verified by measuring only image noise.

Accordingly, it would be desirable to provide a system for facilitating dosage verification where the direct x-ray beam extends beyond the edges of the detector. It would also be desirable to provide such a system without increasing the cost of the system.

BRIEF SUMMARY OF THE INVENTION

These and other objects may be attained in a system which, in one embodiment, utilizes signals from a detector array to determine patient dose. More specifically, the patient dosage is determined by using the detector array signals to determine image noise and a z-axis aperture of a pre-patient collimator. In one embodiment, the pre-patient collimator includes two cams positioned on opposing sides of an x-ray beam radiated from an x-ray source. By altering the position of the cams, the z-axis width and position of the x-ray beam may be altered.

In operation, after determining a maximum signal intensity of a detector cell in the detector array, the position of the cams are altered until the signal intensity at the detector cell is reduced to ½ of the maximum intensity. Utilizing information correlating cam position to aperture size, an adjusted collimator aperture is determined. Using the determined adjusted collimator aperture and image noise, x-ray dose is determined.

By determining the collimator aperture as described above x-ray dose verification is facilitated. In addition, the dose verification is determined without significantly adding to the cost of the system.

BRIEF DESCRIPTION OF THE DRAWINGS

FIG. 3 is a perspective view of a CT system detector array.

FIG. 4 is a perspective view of a detector module.

DETAILED DESCRIPTION OF THE INVENTION

Figure 1:
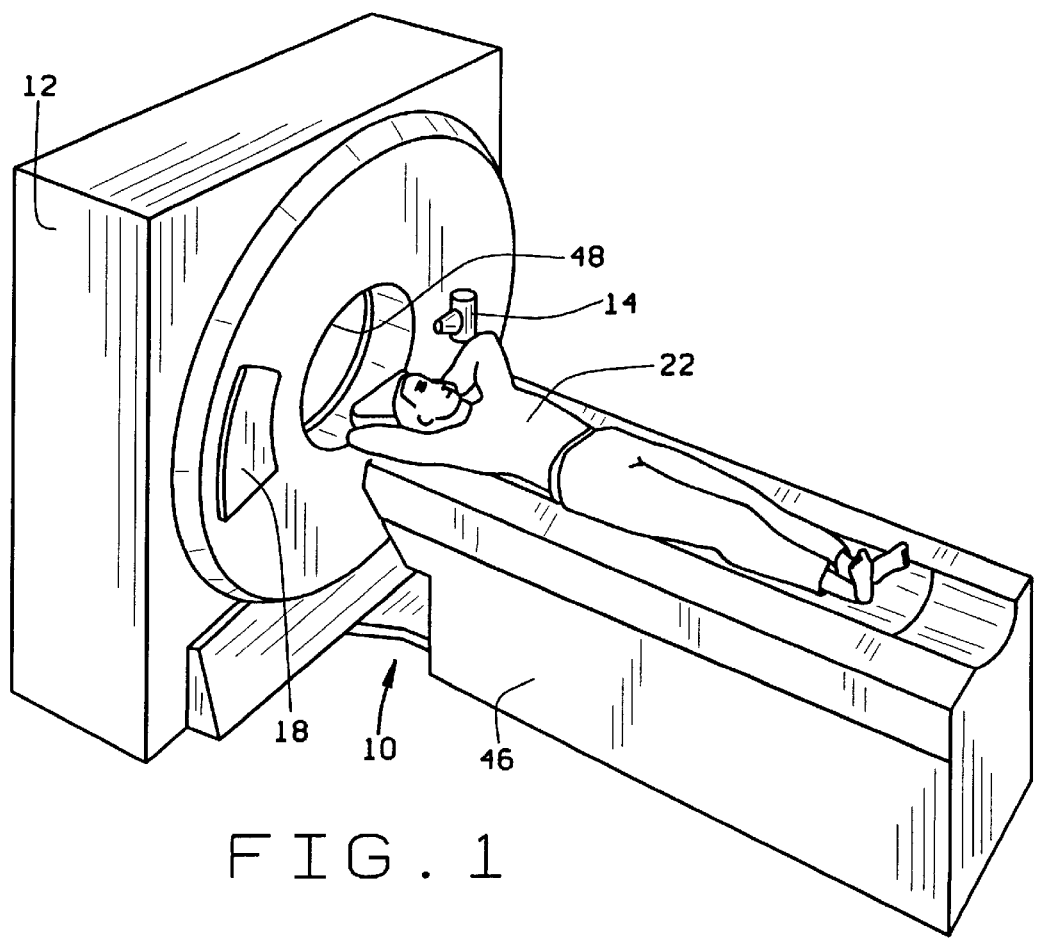
FIG. 1 is a pictorial view of a CT imaging system.
Figure 2:
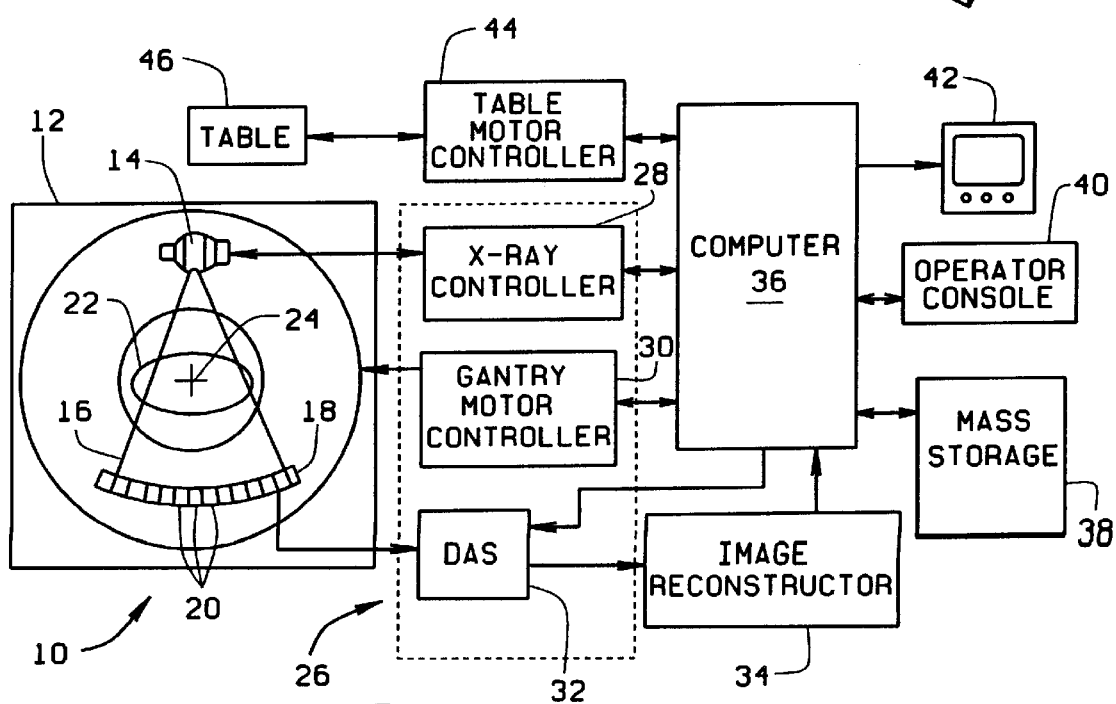
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives and supplies signals via a user interface, or graphical user interface (GUI). Specifically, computer receives commands and scanning parameters from an operator via console 40 that has a keyboard and a mouse (not shown). An associated cathode ray tube display 42 allows the operator to observe the reconstructed image and other data from computer 36. The operator supplied commands and parameters are used by computer 36 to provide control signals and information to x-ray controller 28, gantry motor controller 30, DAS 32, and table motor controller 44.

As shown in FIGS. 3 and 4, detector array 18 includes a plurality of detector modules 58. Each detector module 58 is secured to a detector housing 60. Each module 58 includes a multidimensional scintillator array 62 and a high density semiconductor array (not visible). A post patient collimator (not shown) is positioned over and adjacent scintillator array 62 to collimate x-ray beams before such beams impinge upon scintillator array 62. Scintillator array 62 includes a plurality of scintillation elements arranged in an array, and the semiconductor array includes a plurality of photodiodes (not visible) arranged in an identical array. The photodiodes are deposited, or formed on a substrate 64, and scintillator array 62 is positioned over and secured to substrate 64.

Detector module 58 also includes a switch apparatus 66 electrically coupled to a decoder 68. Switch apparatus 66 is a multidimensional semiconductor switch array of similar size as the photodiode array. In one embodiment, switch apparatus 66 includes an array of field effect transistors (not shown) with each field effect transistor (FET) having an input, an output, and a control line (not shown). Switch apparatus 66 is coupled between the photodiode array and DAS 32. Particularly, each switch apparatus FET input is electrically connected to a photodiode array output and each switch apparatus FET output is electrically connected to DAS 32, for example, using flexible electrical cable 70.

Decoder 68 controls the operation of switch apparatus 66 to enable, disable, or combine the outputs of the photodiode array in accordance with a desired number of slices and slice resolutions for each slice. Decoder 68, in one embodiment, is a decoder chip or a FET controller as known in the art. Decoder 68 includes a plurality of output and control lines coupled to switch apparatus 66 and computer 36. Particularly, the decoder outputs are electrically connected to the switch apparatus control lines to enable switch apparatus 66 to transmit the proper data from the switch apparatus inputs to the switch apparatus outputs. The decoder control lines are electrically connected to the switch apparatus control lines and determine which of the decoder outputs will be enabled. Utilizing decoder 68, specific FETs within switch apparatus 66 are enabled, disable, or combined so that specific outputs of the photodiode array are electrically connected to CT system DAS 32. In one embodiment defined as a 16 slice mode, decoder 68 enables switch apparatus 66 so that all rows of the photodiode array are electrically connected to DAS 32, resulting in 16 separate, simultaneous slices of data being sent to DAS 32. Of course, many other slice combinations are possible.

In one specific embodiment, detector 18 includes fifty-seven detector modules 58. The semiconductor array and scintillator array 62 each have an array size of 16×16. As a result, detector 18 has 16 rows and 912 columns (16×57 modules), which enables 16 simultaneous slices of data to be collected with each rotation of gantry 12. Of course, the present invention is not limited to any specific array size, and it is contemplated that the array can be larger or smaller depending upon the specific operator needs. Also, detector 18 may be operated in many different slice thickness and number modes, e.g., one, two, and four slice modes. For example, the FETs can be configured in the four slice mode, so that data is collected for four slices from one or more rows of the photodiode array. Depending upon the specific configuration of the FETs as defined by decoder control lines, various combinations of outputs of the photodiode array can be enabled, disabled, or combined so that the slice thickness may, for example, be 1.25 mm, 2.5 mm, 3.75 mm, or 5 mm. Additional examples include a single slice mode including one slice with slices ranging from 1.25 mm thick to 20 mm thick, and a two slice mode including two slices with slices ranging from 1.25 mm thick to 10 mm thick. Additional modes beyond those described are possible.

Figure 5:
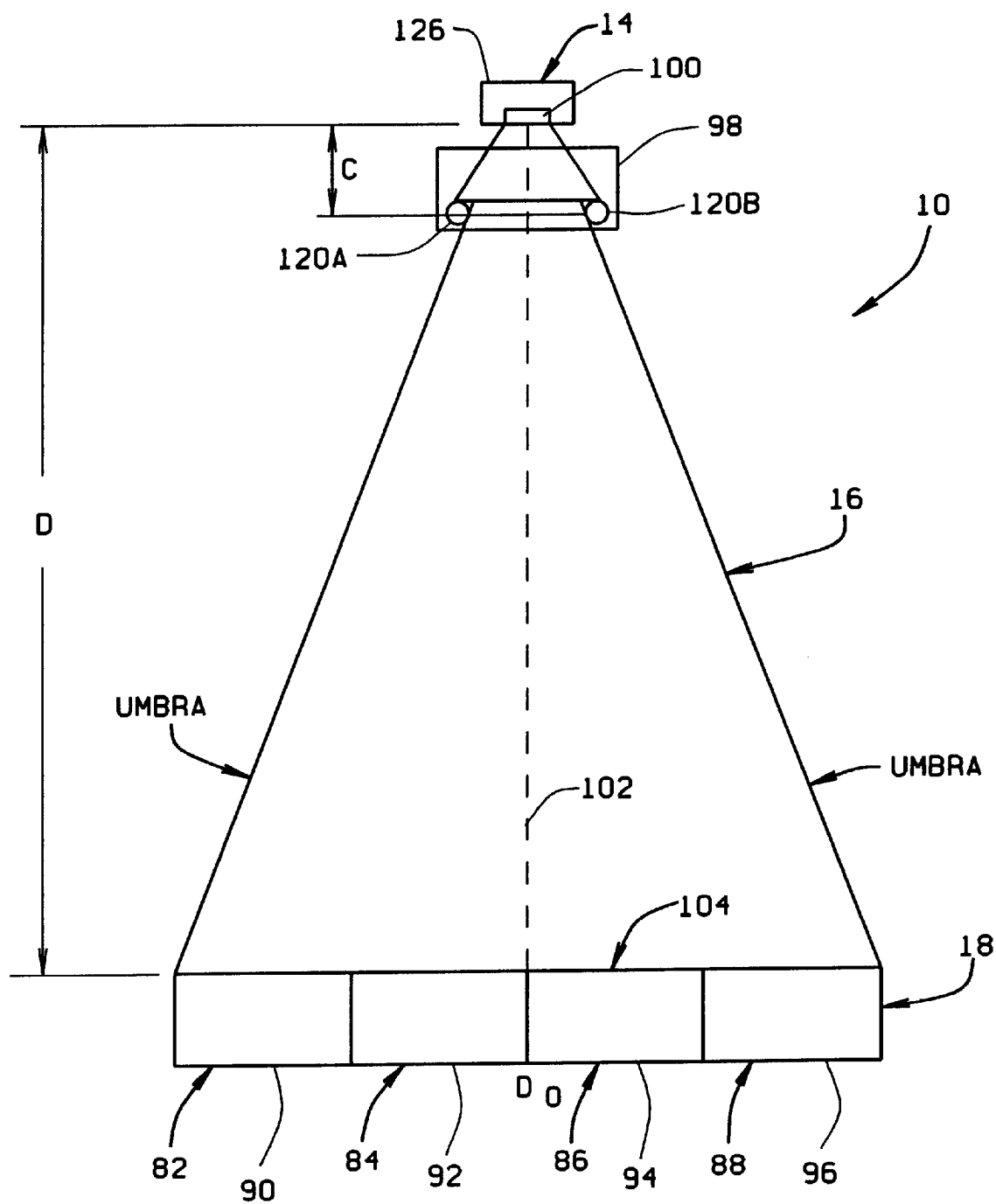
FIG. 5 is a schematic view of the CT imaging system shown in FIG. 1.

FIG. 5 is a schematic view of one embodiment of imaging system 10 in accordance with the present invention. In one embodiment, system 10 is a "four slice" system in that four rows 82, 84, 86 and 88 of detector cells are utilized to obtain projection data. Detector cells 90, 92, 94 and 96, in addition to obtaining projection data, are utilized for determining an aperture (not shown) of a source, or pre-patient collimator 98.

More specifically, and as shown in FIG. 5, x-ray beam 16 emanates from a focal spot 100 of x-ray source 14 (FIG. 2). X-ray beam 16 is collimated by pre-patient collimator 98, and collimated beam 16 is projected toward detector cells 90, 92, 94 and 96. A plane 102, generally referred to as the "fan beam plane", contains the centerline of focal spot 100 and the centerline of beam 16. In FIG. 5, fan beam plane 102 is aligned with the centerline $D_0$ of exposure area 104 on detector cells 90, 92, 94 and 96.

In one embodiment, collimator 98 includes concentric cams 120A and 120B. Cams 120A and 120B are positioned on opposing sides of fan beam plane 102 and may be independently rotated to alter the spacing, or aperture between cams 120A and 120B and their location relative to fan beam plane 102. Cam 120A and 120B are separately driven to a commanded position, in one embodiment, by a stepper motor having a 2000 count encoder (not shown). In one embodiment, the stepper motor and encoder signals are supplied to and from an interface circuit (not shown) which is controlled by x-ray controller 28. Cams 120A and 120B are fabricated from an x-ray absorbing material, for example, tungsten.

As a result of the concentric shape, the rotation of respective cams 120A and 120B alters the z-axis profile of x-ray beam 16. More specifically, altering or changing position of cams 120A and 120B adjusts, or changes the z-axis position and width of x-ray beam umbra. For example, by rotating the stepper motors in opposite directions so that cams 120A and 120B move either together or apart, the total width of x-ray beam umbra is narrowed or widened. Conversely, rotating the stepper motors in the same direction so the spacing between cams 120A and 120B remain the same, the z-axis position of plane 102 is moved relative to detector array 18, specifically, $D_0$. Additionally, altering only the position of cam 120A by rotating the stepper motor coupled to cam 120A, alters the umbra width and position of beam 16 relative to one edge of detector array 18. Similarly, altering the position of cam 120B, alone, alters the umbra width and position relative to the other, or second edge, of detector array 18.

Figure 6:
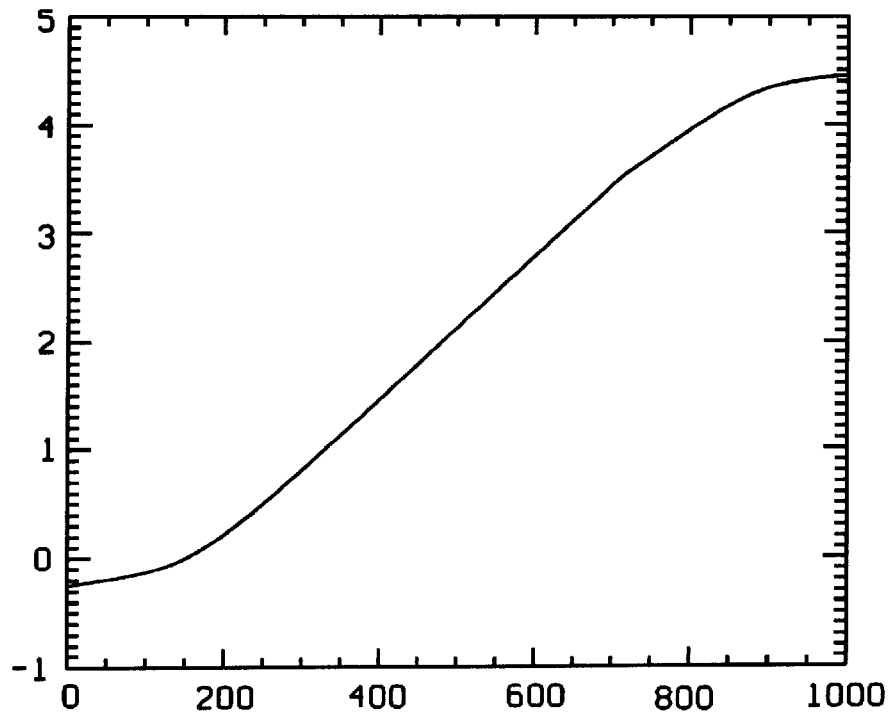
FIG. 6 is a graph illustrating cam position as a function of cam position encoder position.

In one embodiment, during fabrication of system 10, collimator 98 is characterized using, for example, a laser camera to determine the distance from a gantry base plate mounting surface 126 to a center of respective cams 120A and 120B. The respective measured distances for cams 120A and 120B are stored, for example, in a memory of controller 28, so that separate tables of distance and encoder position are generated for respective cams 120A and 120B. The table data represent cam position from a center (mm) as function of cam encoder position, for example, for cam 120A as shown in FIG. 6. During the characterization of cams 120A and 120B, the data collected for each encoder position is verified to conform with theoretical expectations so that the function does not contain bad data points or discontinuities and follows the shape determined by the design parameters. In addition, a distance, C, from source 14 to collimator 98 and a distance, D, from each cell of detector array 18 to source 14 are known from the CT gantry design geometry and are controlled to tight tolerances during manufacturing. During operation, the characterization tables are used to position cams 120A and 120B to the appropriate encode position to obtain a desired nominal aperture and aperture offset.

Figure 7:
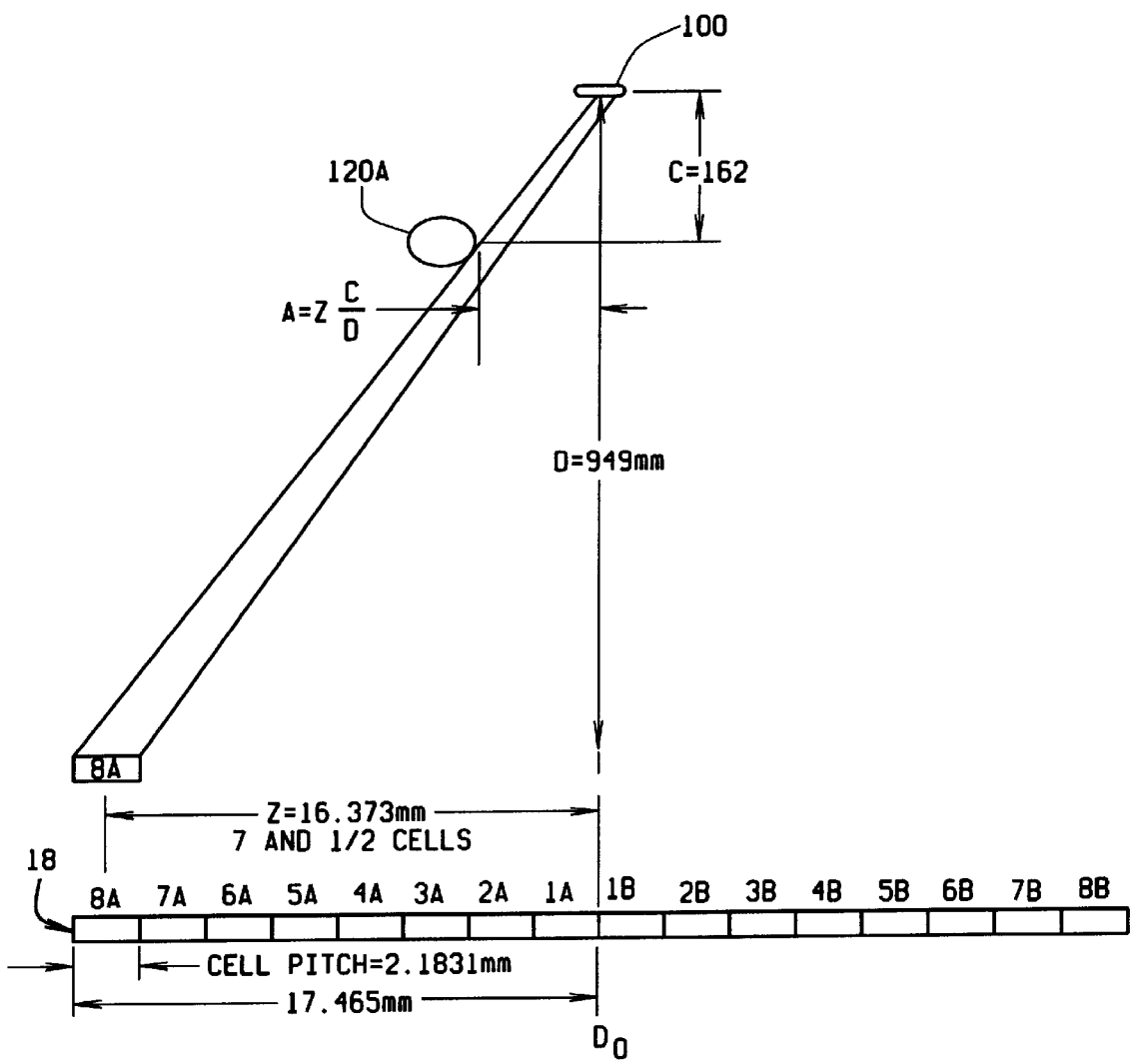
FIG. 7 is a schematic view the CT imaging system shown in FIG. 5.

The cell width and spacing of detector array 18 is controlled to very tight tolerances so that the signal intensities of detector array 18 may be utilized to measure, or determine the aperture of collimator 98. Specifically, cams 120A and 120B are adjusted, or swept, to determine the position where the signal intensity over each detector cell, or channel, is reduced to approximately ½ of a maximum signals intensity. The ½ signal intensity represents the position where collimator 98 is blocking, or collimating, approximately ½ of x-ray beam being radiated from focal spot 100. By utilizing the z-axis width of each detector cell of detector array 18 and the distance between source 14 and collimator 98 and source 14 and detector array 18, an aperture of collimator 98 may be determined. More specifically, for example, the aperture of collimator cam 120A is:

$$A=Z*(C/D),$$

where Z is a distance from a center of the detector cell generating the ½ of the maximum signal intensity to the center of detector array 18, or $D_0$ More specifically, distance Z is the cell pitch, or z-axis width, times the number of cells from the centerline of detector array 18 minus ½. For example and as shown in FIG. 7 illustrating a sixteen slice configuration, where C=162 mm, D=949 mm, each cell of detector array 18 has a z-axis width of 2.1831 mm, and the signal intensity of cell 8A is ½ of the maximum signal, the aperture of cam 120A is:

(2.1831 mm * (8–½)) * (162/949)=2.795 mm. The aperture of cam 120B is determined in a similar manner so that an adjusted total aperture may be determined by adding cam 120A aperture and 120B aperture. More specifically, the adjusted aperture of collimator 98 is determined by measuring how far cams 120A and 120B must be moved, or offset, so that beam 16 lies over a center of a detector cell. The distance between the cell center at the aperture plus the change, or offset, in cam 120A position plus the change, or offset, in cam 120B position provides the adjusted aperture of collimator 98.

Although focal spot 100 may become misaligned with the centerline of detector array 18 due to thermal drift and plane of rotation (POR) tube misalignment, the error due to the absolute position of focal spot 92 position will add to one cam aperture and subtract from the other cam position. As a result, the aperture may be determined by the difference between location of cam 120A and cam 120B. In addition, the aperture determined is dependent on the response from individual cells, or channels. In order to minimize the error, intensity signals may be obtained from a plurality of cells, or channels. For example, values may be collected from 100 channels over the isocenter of detector array 18. As a result, any error due to a non-uniform detector response or non-uniform focal distribution function in the z-axis will be offset in the determined positions of cams 120A and 120B.

Figure 8:
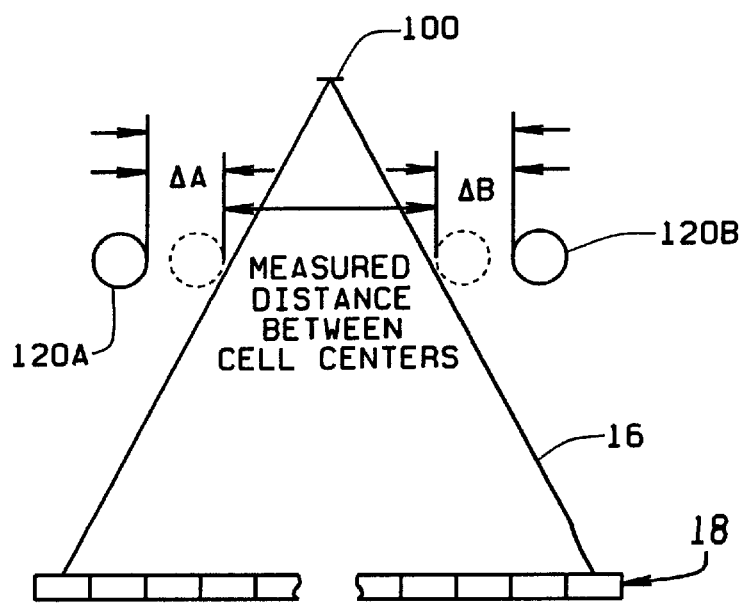
FIG. 8 is a schematic representation of the CT system illustrating the collimator aperture measurement.

The distance between cell centers at the aperture plus the change in position of cams 120A and 120B determines the cam aperture and verifies that the characterization table is properly matched to collimator 98. For example, as shown in FIG. 8, the measured aperture equals the change in position of cam 120A plus the change in the position of cam 120B plus the measured distance between cell centers.

In operation, a reference object, for example a 20 cm water phantom, is scanned and a reconstructed image is generated in a manner known in the art. An image noise is then determined, for example as known in the art, by generation of a standard deviation relative to the mean over a uniform region of pixels for the reference object. The relationship between image noise and dose is established by calibration to certified dosimetry instruments over a statistically significant number of systems. Dosage is then verified by determining that both the image noise and the aperture of collimator 98 are within acceptable limits. Specifically, utilizing the proportional relationship between total x-ray dose and collimator aperture, the x-ray dose may be indirectly determined and verified In one embodiment, system 10 adjusts an aperture of collimator 98 so that edges of x-ray beam umbra is properly positioned over detector array 18. More specifically, using the stepper motors, cams 120A and 120B are positioned so that aperture of collimator is properly adjusted, or sized. Using the encoder signals to determine the position of cams 120A and 120B, aperture of collimator 98 is determined so that x-ray dosage is determined. As a result, the considerable expense of providing dosimetry equipment and procedures for manufacturing and field service may be avoided.

The above described imaging system facilitates x-ray dose verification using the intensity signals from the detector array. In addition, the dose verification is determined without adding to the cost or complexity of the system.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. Similarly, while the systems described herein have been two-slice and four-slice, any multi-slice system may be used. Accordingly, the spirit and scope of the invention are to be limited only by the terms of the appended claims.

What is claimed is:

1. A method of determining x-ray dose in an imaging system, the imaging system including a detector array having at least two rows of detector cells displaced along a z-axis, an x-ray source for radiating an x-ray beam toward the detector array and an adjustable collimator, said method comprising the steps of:

scanning an object;

determining an image noise of the scanned object; and determining a collimator z-axis aperture using the detector array.

2. A method in accordance with claim 1 wherein determining the collimator aperture comprises the steps of:
   positioning the collimator aperture to a nominal value; and
   determining an adjusted collimator aperture.

3. A method in accordance with claim 1 wherein determining the adjusted collimator aperture comprises the step of characterizing the collimator.

4. A method in accordance with claim 1 wherein the detector is a multislice detector.

5. A method in accordance with claim 3 wherein determining the adjusted collimator aperture further comprises the step of measuring the collimator aperture.

6. A method in accordance with claim 5 wherein the x-ray beam is radiated from a focal spot and the collimator includes at least two adjustable cams positioned on opposing sides of the x-ray beam for altering the z-axis profile of the x-ray beam, and wherein measuring the collimator aperture comprises the steps of:
   determining a maximum signal intensity from at least one detector cell; and
   determining a position of the collimator cam wherein the signal intensity at the detector cell is one-half of the maximum signal intensity.

7. A method in accordance with claim 6 wherein determining a position of the collimator cam wherein the signal intensity is one-half of the maximum signal intensity at the detector cell comprises the steps of:
   altering the position of the collimator cam; and
   measuring the detector cell intensity.

8. A method in accordance with claim 7 wherein altering the position of the collimator cam comprises the step of determining a distance from the center of the detector array to the center of the detector cell having one-half intensity.

9. A method in accordance with claim 8 wherein the distance from the center of the detector array to the center of the detector cell having one-half intensity is:
   Z=width of the detector cell * (number of cells with full intensity from the center of the detector array +½).

10. A method in accordance with claim 8 wherein the position of the collimator cam is:

$A = Z^*(C/D)$.

11. A system for determining x-ray dose in an imaging system, the imaging system including a detector array having at least two rows of detector cells displaced along a z-axis, an x-ray source for radiating an x-ray beam toward the detector array and an adjustable collimator, said system configured to:
   scan an object;
   determine an image noise of the scanned object; and
   determine a collimator z-axis aperture using the detector array.

12. A system in accordance with claim 11 wherein to determine the collimator aperture, said system configured to:
   position the collimator to a nominal aperture; and
   determine an adjusted collimator aperture.

13. A system in accordance with claim 11 wherein the detector is a multislice detector.

14. A system in accordance with claim 12 wherein to determine the adjusted collimator aperture, said system configured to characterize the collimator.

15. A system in accordance with claim 12 wherein to determine the adjusted collimator aperture, said system further configured to measure the collimator aperture.

16. A system in accordance with claim 15 wherein the x-ray beam is radiated from a focal spot and the collimator includes at least two adjustable cams positioned on opposing sides of the x-ray beam for altering the z-axis profile of the x-ray beam, and wherein to measure the collimator aperture, said system configured to:
   determine a maximum signal intensity from at least one detector cell; and
   determine a position of the collimator cam where the signal intensity at the detector cell is one-half of the maximum signal intensity.

17. A system in accordance with claim 16 wherein to determine a position of the collimator cam where the signal intensity is one-half of the maximum signal intensity at the detector cell, said system configured to:
   alter the position of the collimator cam; and
   measure the detector cell intensity.

18. A system in accordance with claim 17 wherein to alter the position of the collimator cam, said system configured to determine a distance from the center of the detector array to the center of the detector cell having one-half intensity.

19. A system in accordance with claim 18 wherein said distance from the center of the detector array to the center of the detector cell having one-half intensity is:
   Z=width of the detector cell * (number of cells with full intensity from the center of the detector array +½).

20. A system in accordance with claim 19 wherein said position of the collimator cam is:

$A = Z^*(C/D)$.

21. An imaging system comprising a multislice detector array having at least two rows of detector cells displaced along a z-axis, an x-ray source for radiating an x-ray beam toward the detector array, a pre-patient collimator having an aperture said system configured to:
   scan an object;
   determine image noise of the scanned object; and
   determine a collimator z-axis aperture using the detector array.

22. An imaging system in accordance with claim 21 wherein to determine said collimator aperture, said imaging system configured to:
   characterize said collimator; and
   measure said collimator aperture.

23. A system in accordance with claim 21 wherein said x-ray beam is radiated from a focal spot and said collimator includes at least two adjustable cams positioned on opposing sides of said x-ray beam for altering the z-axis profile of said x-ray beam, and wherein to measure said collimator aperture, said system configured to:
   determine a maximum signal intensity from at least one detector cell; and
   alter said collimator cam position until said detector cell signal intensity is one-half of the maximum signal intensity.

24. A system in accordance with claim 23 wherein to alter said position of said collimator cam, said system configured to determine a distance from the center of said detector array to the center of said detector cell having one-half intensity.

25. A system in accordance with claim 24 wherein said distance from the center of said detector array to the center of said detector cell having one-half intensity is:
   Z=width of said detector cell * (number of cells with full intensity from the center of said detector array +½).

26. A system in accordance with claim 25 wherein said position of said collimator cam is:

$A = Z^*(C/D)$.

* * * * *

UNITED STATES PATENT AND TRADEMARK OFFICE
CERTIFICATE OF CORRECTION

PATENT NO. : 6,141,402
DATED : October 31, 2000
INVENTOR(S) : Thomas L. Toth

Page 1 of 1

It is certified that error appears in the above-identified patent and that said Letters Patent is hereby corrected as shown below:

Claim 19, Column 8:
Line 23, delete "fill" and substitute -- full --.

Signed and Sealed this

Twelfth Day of June, 2001

Attest:

NICHOLAS P. GODICI
Attesting Officer  Acting Director of the United States Patent and Trademark Office

UNITED STATES PATENT AND TRADEMARK OFFICE
CERTIFICATE OF CORRECTION

PATENT NO.   : 6,141,402
DATED        : October 31, 2000
INVENTOR(S)  : Thomas L. Toth It is certified that error appears in the above-identified patent and that said Letters Patent is hereby corrected as shown below:

<u>Claim 19, Column 8,</u>
Line 23, delete "fill" and substitute -- full --.

Signed and Sealed this

Twenty-sixth Day of June, 2001

*Attest:*

*Attesting Officer*

NICHOLAS P. GODICI
*Acting Director of the United States Patent and Trademark Office*